(12) United States Patent
Hochhalter

(10) Patent No.: US 11,185,708 B2
(45) Date of Patent: Nov. 30, 2021

(54) HEARTSTATION REMOTE MONITOR SYSTEM

(71) Applicant: RescueStat LLC, Meridian, ID (US)

(72) Inventor: Keith Hochhalter, Inverness, IL (US)

(73) Assignee: RescueStat LLC, Meridian, ID (US)

( * ) Notice: Subject to any disclaimer, the term of this patent is extended or adjusted under 35 U.S.C. 154(b) by 0 days.

(21) Appl. No.: 15/787,412

(22) Filed: Oct. 18, 2017

(65) Prior Publication Data

US 2019/0111272 A1 Apr. 18, 2019

(51) Int. Cl.
*A61N 1/39* (2006.01)
*H02M 3/07* (2006.01)
*A61N 1/04* (2006.01)
*G07C 3/00* (2006.01)

(52) U.S. Cl.
CPC ......... *A61N 1/3925* (2013.01); *A61N 1/3904* (2017.08); *G07C 3/00* (2013.01)

(58) Field of Classification Search
CPC .......... A61N 1/37; A61N 1/39; A61N 1/3708; A61N 1/3925; A61N 1/04; A61N 1/046; A61N 1/0492; A61N 1/0484; A61B 5/6805
See application file for complete search history.

(56) References Cited

U.S. PATENT DOCUMENTS

| | | | |
|---|---|---|---|
| 5,879,374 A | 3/1999 | Powers et al. | |
| 6,366,809 B1 * | 4/2002 | Olson | A61N 1/3975 607/29 |
| 7,120,488 B2 | 10/2006 | Nova et al. | |
| 7,570,994 B2 | 8/2009 | Tamura et al. | |
| 8,116,863 B2 | 2/2012 | Vaisnys et al. | |
| 8,498,701 B2 | 7/2013 | Vaisnys et al. | |

(Continued)

FOREIGN PATENT DOCUMENTS

| AU | 2007203529 B2 | 8/2012 |
|---|---|---|
| CN | 104548350 A | 4/2015 |

(Continued)

OTHER PUBLICATIONS

European Patent Application No. 18199800.6, Extended Search Report, dated Jan. 3, 2019, 9 pages.

*Primary Examiner* — Jon Eric C Morales

(57) ABSTRACT

An automated external defibrillator (AED) and AED Monitoring system made up of an AED, the AED having a self-diagnostic subroutine and performing said subroutine at regular intervals, the AED having at least an audio indicator that indicates the results of the self-diagnostic when the diagnosis is that the AED is in need of maintenance and a remote AED monitoring system, the AED monitoring system having an electromagnetic coil, microphone, battery, microprocessor, and wireless communication device, wherein the microprocessor selectively powers up the AED monitoring system prior to the AED's self-diagnostic subroutine and utilizes the electromagnetic coil and microphone to monitor for the AED's audio indicator that the AED is in need of maintenance, and the microprocessor transmitting a wireless signal through the wireless communication device indicating whether the AED is in need of maintenance; the microprocessor selectively powering down the AED monitoring system after transmitting the wireless signal.

19 Claims, 5 Drawing Sheets

(56) References Cited

U.S. PATENT DOCUMENTS

| | | |
|---|---|---|
| 9,008,767 B2 | 4/2015 | Bowers |
| 9,861,806 B2* | 1/2018 | Kaib ................. A61N 1/046 |
| 10,426,946 B2 | 10/2019 | Macho et al. |
| 10,773,091 B2 | 9/2020 | Andrews et al. |
| 10,924,553 B2 | 2/2021 | Durrant et al. |
| 2008/0097546 A1* | 4/2008 | Powers ............. A61B 5/0424 |
| | | 607/36 |
| 2009/0149894 A1 | 6/2009 | Merry et al. |
| 2014/0097964 A1 | 4/2014 | Massmann |
| 2017/0003356 A1* | 1/2017 | Kaib ................ G01R 31/3679 |
| 2018/0140859 A1* | 5/2018 | Meir .................. A61N 1/3981 |
| 2019/0015672 A1 | 1/2019 | Halsne |
| 2019/0232070 A1 | 8/2019 | Lancaster et al. |

FOREIGN PATENT DOCUMENTS

| | | |
|---|---|---|
| FR | 2946539 A1 | 12/2010 |
| KR | 20150062430 B1 | 6/2015 |
| TW | M478517 U | 5/2014 |
| WO | 2017162627 A1 | 9/2017 |

\* cited by examiner

HEARTSTATION REMOTE MONITOR SYSTEM

FIELD OF THE INVENTION

The present invention generally relates to automatic external defibrillators (AEDs) and devices and systems related to the monitoring and diagnostics thereof.

BACKGROUND

The Automated External Defibrillators (AEDs) are used all over the world in locations such as health clubs, airports, schools, churches, office buildings, etc. Often, these systems are intended to be installed in permanent and semi-permanent displays, but are also carried in bags by Emergency Medical Technicians (EMTs). AEDs are generally powered by primary lithium batteries with a life of 1 to 4 years. AEDs also require pads that have a limited life and must be replaced if used in a life saving event before the expiration date. At the time of purchase and installation of these devices, those maintaining the devices have good intentions regarding the regular maintenance required to keep them operational, however with the turnover of personnel managing these devices, and over time with this being a limited responsibility for those assigned, they are quickly forgotten. This often leads to negative consequences. AEDs hang on walls with dead batteries, expired pads, and in faulty conditions. Fire departments, the FDA, and AED distributors report that a large percentage of these devices are forgotten within 5 years and left for dead. Multiple lawsuits have resulted from rescue attempts with dead or faulty devices.

While no system can expect perfection, many AED monitors have yet to come into the 21st century. These stations are, at best, monitored by visual inspection of untrained (or barely trained) personnel who log the diagnostic condition using pen and paper. Such records are easy to lose, and are not easily accessible. In addition, without a good secondary checking mechanism, entire AEDs are lost when a paper record is lost. In addition, when personnel changes or things get busy, these inspections are often forgotten.

Several large distributors of AEDs attempt to support their customers in the maintenance of AEDs with software that notifies the safety personnel in charge of the AEDs when it is time to replace pads and batteries. This is strictly done by time on a spreadsheet, and does not actually monitor what is going on with the AED. The AEDs do a daily, weekly, and monthly self test to determine if maintenance is required. If they determine that a problem has occurred they start beeping and display an indicator on the front of the AED that varies by AED, all in hope that a passerby notices and responds to its request for maintenance. This is unlikely if stored in a cabinet or closet unless the safety program requires a visual inspection that is adhered to.

U.S. Pat. No. 8,565,871 ('871 Patent), which issued to Tuysserkani, discloses an Automated External Defibrillator Device with Integrated Wireless Modem. The '871 Patent describes automatic external defibrillator (AED) includes an integral wireless modem configured so that, upon activation, the AED automatically connects to a wireless network and reports the event to an emergency services center or remote server to call for an ambulance. The activation report may be accomplished by calling an emergency services center and playing a prerecorded voice message that includes AED location information. Alternatively, the activation report may be transmitted via a wireless data network to a remote server which routes the information to appropriate authorities. After the activation report is transmitted, the AED may transmit patient and treatment data to the server. The AED may include a speaker phone capability so a caregiver can talk with a dispatcher or medical team. The AED may also automatically report activation data and periodic self-diagnostic testing results to a manufacturer or service provider via a wireless data call to a remote server.

U.S. Pat. No. 8,854,194 ('194 Patent), which issued to McSheffrey et al., discloses Remote Monitoring. The '194 Patent essentially describes remote monitoring and inspection of measurement devices, emergency equipment, parking spaces, and other items is accomplished by using an image sensor (e.g., a CMOS sensor) to capture an image containing information about the monitored item. A signal containing information about the image (e.g., data representing the captured image or data indicating the state of the captured image) is transmitted to a remote central station.

U.S. Pat. No. 9,220,912 ('912 Patent), which issued to Elghazzawi, discloses Medical Equipment Servicing. The '912 Patent describes Systems and techniques for centralized management and servicing of medical equipment such as automated external defibrillators (AEDs) are described herein. The systems and techniques for receiving status updates from multiple automated external defibrillators, receiving, from a user, a request to access status information, and sending, to the user, summary level status information for at least some of the multiple automated external defibrillators, the summary level status information being grouped based on a measure of geographic proximity of the multiple automated external defibrillators.

U.S. Pat. No. 9,295,849 ('849 Patent), which issued to Elghazzaiw describes Medical Equipment Messaging. The '849 Patent describes medical equipment messaging.

United States Patent Application No. Re. 20110060378, which is authored by Tuysserkani, teaches an automatic external defibrillator (AED) includes an integral wireless modem configured so that, upon activation, the AED automatically connects to a wireless network and reports the event to an emergency services center or remote server to call for an ambulance. The activation report may be accomplished by calling an emergency services center and playing a prerecorded voice message that includes AED location information. Alternatively, the activation report may be transmitted via a wireless data network to a remote server which routes the information to appropriate authorities. After the activation report is transmitted, the AED may transmit patient and treatment data to the server. The AED may include a speaker phone capability so a caregiver can talk with a dispatcher or medical team. The AED may also automatically report activation data and periodic self-diagnostic testing results to a manufacturer or service provider via a wireless data call to a remote server.

The problems with these systems, and others, are addressed by the present invention and discussed in greater detail below.

BRIEF SUMMARY

Currently available AEDs lack many of the proposed features described below. An optimal solution would be to have a means to identify when an AED goes into a fault mode and to report the problem remotely to a monitoring system. This system would then report the problem to a person that can maintain the device without the regular, physical presence of the person with the AED. Preferably, one approach would be applicable to all AEDs despite various indicators of failure and various locations of these indicators on the AEDs. A further goal would be to have the solution be a retrofit to all existing AED cabinets and not only new cabinets. An even further goal would be to have the device operate on batteries, capable of at least a 5 year operation.

It is possible to use a camera as a way to monitor an AED in its cabinet. However, challenges with this approach are in being able to accommodate multiple indicators with various AEDs. Different color and shape indicators are used. The most popular just uses a blinking green LED. Some are in dark locations. Some AEDs are the same colors as the indicators (greens and reds). Complex analysis would be required to distinguish a fault condition without user interaction. Also, most AEDs have their faces right against the door of the AED cabinet so there is not room for a camera in existing cabinets. Additionally the camera would likely have to be setup on the door and because AEDs come in various sizes camera alignment would be tedious. Additionally, a camera requires a significant amount of electricity to operate, resulting in battery drain.

Thus, the present monitoring system utilizes certain features of AEDs to monitor them and report their condition to a remote system. All AEDs turn on at a selected interval for a self inspection. Most turn on every 24 hours for a quick check, every week for a more thorough self inspection, and every month for a complete inspection. These inspections not only check the batteries and pads, but also the internal functions of the AED including the charge circuitry. Following these inspections a pass or fail visual indicator is set, as well as a periodic beep in a fault state.

Utilizing the inherent diagnostics of modern AEDs, the current invention therefore is able to monitor the state of an AED without using significant power, which would result in battery drain. The basic method to achieve this result is as follows: 1) Wake up the monitoring system just prior to scheduled AED self inspection; 2) Sense the turn on of the AED for its self inspection; 3) Listen for a fault signal for a defined period of time, and if the fault signal is discovered a fault condition is present; 4) Report via wireless communication (Wi-Fi, Bluetooth, cellular, etc) the outcome of monitoring; 5) Return monitoring system to battery conservation, sleep mode.

While the above steps are, themselves, novel, there are additional innovations set forth in this disclosure that allow for more accurate and specific monitoring of AEDs. Functionally, most AED cabinets do not have line power (AC outlets) to power the battery of a monitoring system. However, the minimum life goal of the battery for an AED monitor is 5 years. Therefore, a very low power microcontroller is used that has the capability to go into a deep sleep consuming only enough power to watch a timer programmed to wake up the device just prior to the scheduled self inspection of the AED. Each version of AED has a hard coded, defined time for its inspection. For example, all Cardiac Science G3 AEDs do a self check at 3:03 AM. This time can be hard coded into the AED monitor on installation, but the system also has a diagnostic method that lets an installed AED monitor discover the diagnostic setting of the AED it is monitoring with no user input.

One component of the sensing system, for sensing the AED powering up for its self-inspection, is a large diameter, multi-turn coil. This coil senses the electromagnetic field generated by the AED when it powers on for diagnostics. A microcontroller will monitor the coil at the time of the status check to verify that the AED is present and that the AED battery is not dead. If coil signal is not observed a fault status for a missing or dead battery is sent via wireless communications to an online monitoring system. Knowing that the AED is present and powered, the microcontroller then uses a microphone and waits for a series of beeps at a defined frequency for a defined period of time for the specific AED (these can be pre-programmed or learned by the AED monitor). During this period if the specific set of beeps are observed, the AED is in fault mode and needs maintenance. If not, the AED has passed its self inspection. The wireless system can send a myriad of messages to the central monitoring system including: 1) AED missing or dead battery; 2) AED in fault mode; 3) AED operational. In addition, it is contemplated that the central monitoring system will indicate a breakdown after a certain number of hours of inactivity. Thus, the following are proposed to alleviate such problems:

In a first embodiment an combination automated external defibrillator (AED) and AED Monitoring system is proposed. The combination made up of an AED, the AED having a self-diagnostic subroutine and performing said subroutine at regular intervals, the AED having at least an audio indicator that indicates the results of the self-diagnostic when the diagnosis is that the AED is in need of maintenance; and a remote AED monitoring system, the AED monitoring system having a microphone, battery, microprocessor, and wireless communication device, wherein the microprocessor selectively powers up the AED monitoring system prior to the AED's self-diagnostic subroutine and utilizes the microphone to monitor for the AED's audio indicator that the AED is in need of maintenance, and the microprocessor transmitting a wireless signal through the wireless communication device indicating whether the AED is in need of maintenance; the microprocessor selectively moving the AED monitoring system from an activated state to a low power state after transmitting the wireless signal.

In another embodiment the disclosure contemplates a method for monitoring and reporting the state of an automated external defibrillator (AED). The method comprised of providing an AED and an AED monitor; detecting a signal from the AED to establish a time and an interval when the AED conducts a self-diagnostic test; placing the AED monitor in a low power state; maintaining the AED monitor in a low power state; powering up the AED monitor into an active state at a selected time before the AED conducts the self-diagnostic test; detecting an electromagnetic signal from the AED; detecting an audible beep from the AED; wirelessly reporting a state of the AED to an online monitoring system, the state of the AED determined by the electromagnetic signal from the AED and the audible beep from the AED; and returning the AED monitor to the low power state.

In another embodiment the disclosure contemplates a remote monitor for an automated external defibrillator. The remote monitor comprising a case; an antenna; a microphone; a battery; an electromagnetic coil; and a microprocessor connected to and receiving input from the antenna, microphone, and electromagnetic coil, the microprocessor receiving power from the battery selectively outputting signals over the antenna; and wherein the microprocessor capable of selectively activating and deactivating the remote monitor at a selected interval and time, the selected interval and time corresponding to Such embodiments do not represent the full scope of the invention. Reference is made therefore to the claims herein for interpreting the full scope of the invention. Other objects of the present invention, as well as particular features, elements, and advantages thereof, will be elucidated or become apparent from, the following description and the accompanying drawing figures.

DESCRIPTION OF THE DRAWINGS

The present invention may be better understood, and its numerous objects, features, and advantages made apparent to those skilled in the art by referencing the accompanying drawings.

DETAILED DESCRIPTION

Referring now the drawings with more specificity, the present invention essentially discloses a device for monitoring an automatic external defibrillator (AED). The preferred embodiments of the present invention will now be described with reference to FIGS. 1-5 of the drawings. Variations and embodiments contained herein will become apparent in light of the following descriptions.

Figure 1:
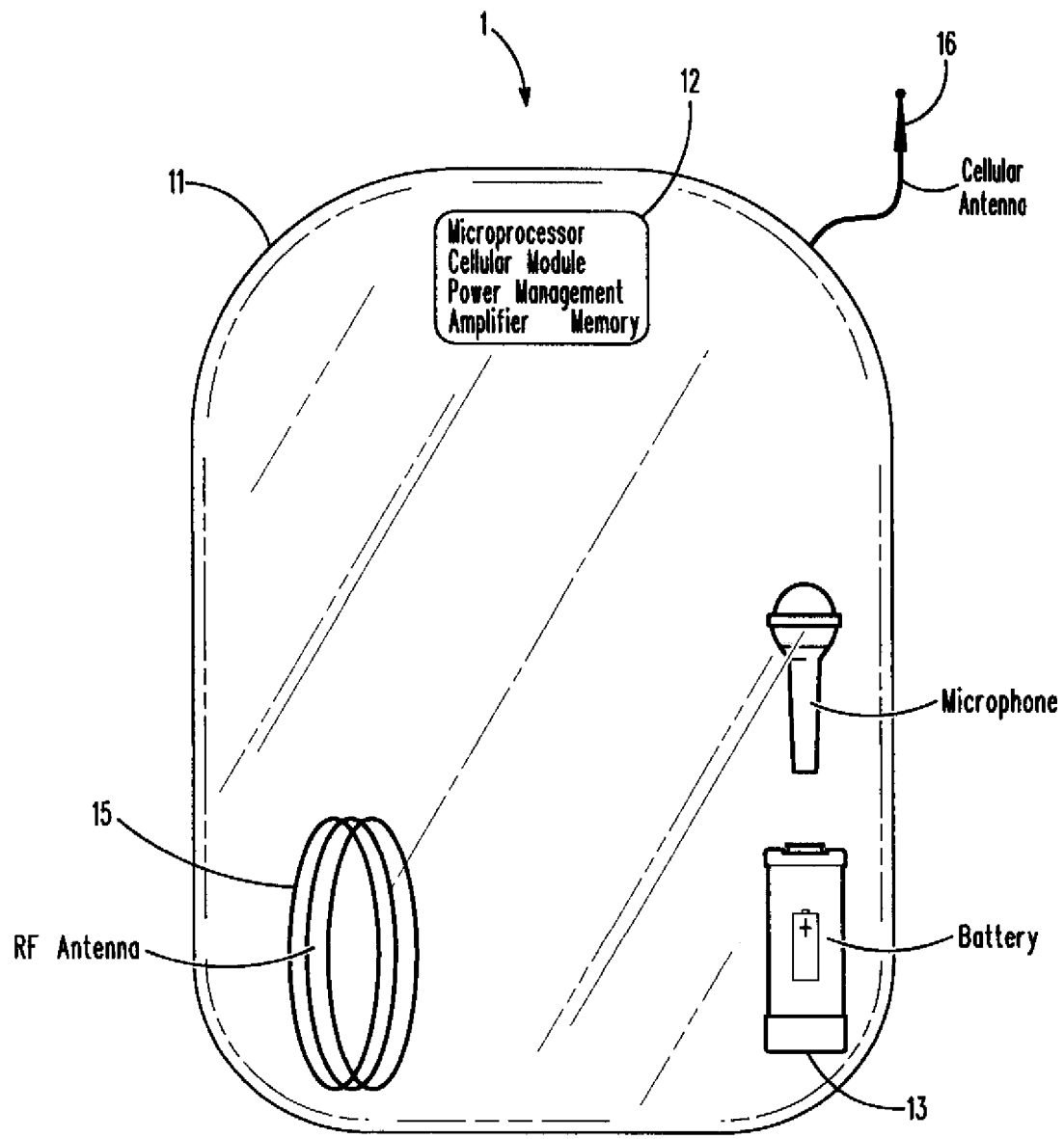
FIG. 1 is a front view of a remote monitor according to the present disclosure.

Looking now to FIG. 1, an AED monitor 1 is shown. Preferably the AED monitor will have an exterior case 11 which is approximately 3.5"×3.5"×0.5" but smaller and larger devices are also contemplated. The case 11 contains the remaining components of the AED monitor 1. The AED monitor 1 contains a microprocessor 12 that is connected to the remaining components of the AED monitor and essentially controls the operation of AED monitor 1. The monitor 1 is powered by at least one battery 13. The battery life of the AED monitor 1 is a key feature of the present invention. The battery 13 should be capable of remaining in operation long enough such that the AED monitor's battery 13 does not run out until the AED itself needs to be replaced and/or have the AED batteries replaced. The battery life is typically improved by placing the AED monitor 1 into a low-power state at certain points of the day. The AED monitor also has at least two sensing mechanisms: a microphone 14 and an electromagnetic coil 15. Both are preferably internally situated so as to resist damage. The Microphone 14 is configured to listen for beeps from an AED which indicate when the AED has failed an internal diagnostic test. The coil 15 is typically a radio frequency coil, more specifically a multi-turn coil, the coil is thus capable of sensing an electromagnetic field generated by the AED. The AED monitor communicates via an antenna 16, being a cellular, Bluetooth, or other wireless communication antenna. While for some operations an internal antenna 16 is preferable, in certain applications (such as when the AED is placed into a metallic cabinet), it is preferable to have the antenna extend beyond case 11 and to be mounted to the exterior of an AED cabinet (see, e.g. FIG. 3).

Figure 2:
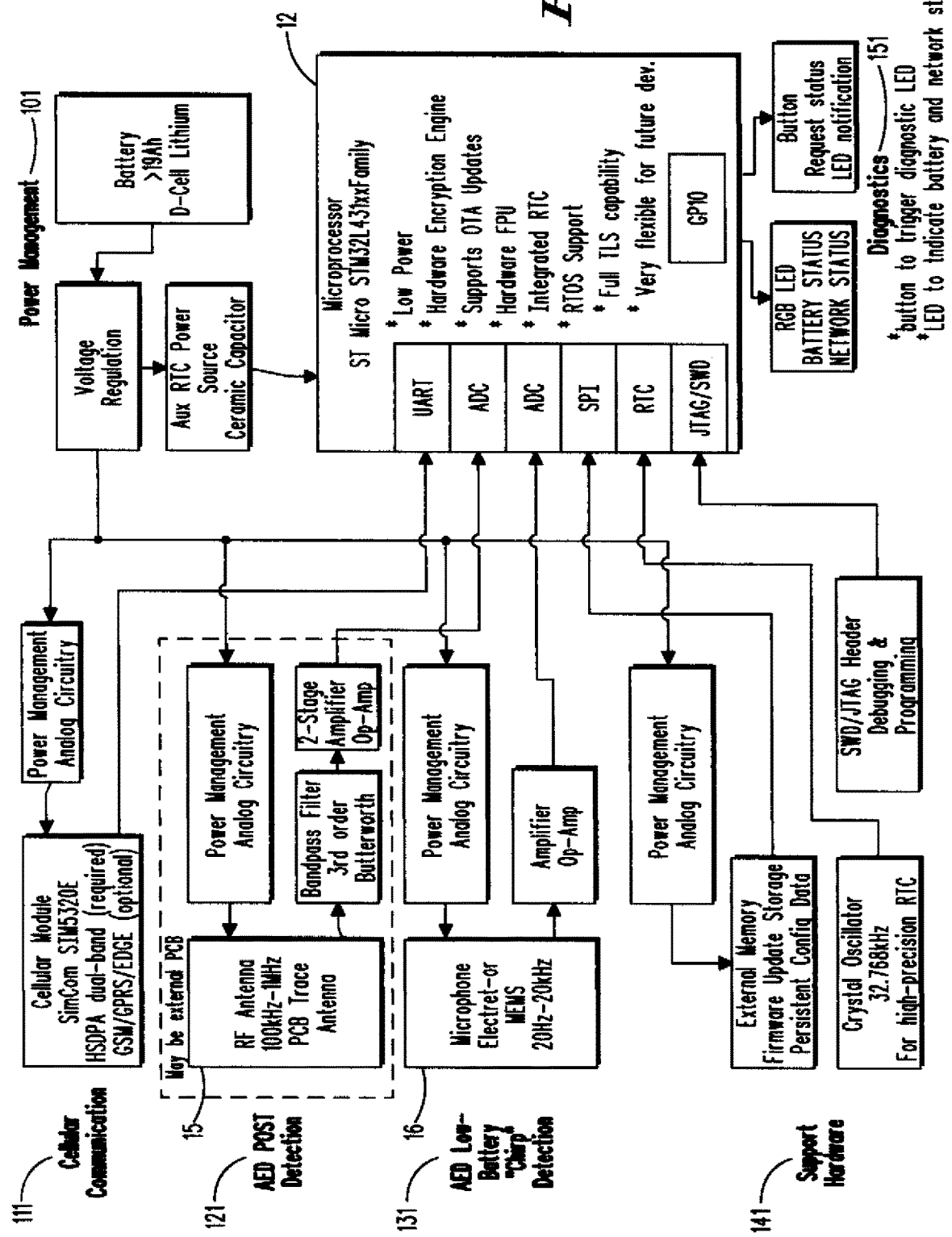
FIG. 2 is an electrical schematic of the remote monitoring system according to the present disclosure.

Having describe the general components of AED monitor 1, we now turn to FIG. 2 for a more detailed schematic of the workings of AED monitor 1. Generally, power management processes 101 communicate with microprocessor 12, the cellular communication 111, AED post detection 121, chirp detection 131, and the support hardware 141. The power management 101 typically will consists of a battery such as a lithium ion battery connected to a voltage regulator. As shown an aux RTC (real time clock) power source connects the power management to the microprocessor 12. One skilled in the art may substitute or implement other suitable substitutes for powering the AED monitor 1.

Looking now to the cellular communication systems 111, they are typically composed of power management circuitry and a cellular module. The communication devices, as shown can be SimCon (™) or other similar link, however it should have HSDPA dual-band capabilities, while other protocols such as GSM/GPRS/EDGE capabilities may be preferred for certain applications. The cellular communications 111 report to a universal asynchronous receiver-transmitter (UART) or analogous part on the microprocessor 12.

The AED POST detection 121 systems generally relate to electromagnetic coil (or RF antenna) 15. The electromagnetic coil 15 is preferably a 100 kHz-1 MHz PCB trace antenna for detecting electromagnetic fields emanating from the AED. Preferably a bandpass filter (e.g. 3rd order Butterworth) will filter the analogue input from the antenna. The signal may also need amplification (e.g. 2-stage Op-Amp) before reporting the signal to an analogue-to-digital converter (ADC) on the microprocessor 12.

Similarly, the AED low-battery aka "chirp" detection 131 systems generally relate to Microphone 16. The microphone 16 is preferably a microphone electret or MEMS for detecting beeps, chirps, and other sounds emitted by the AED. The signal may also need amplification (e.g. Op-Amp) before reporting the signal to an analogue-to-digital converter (ADC) on the microprocessor 12.

Other Support hardware 141 is discussed herein, such hardware may be implemented on microprocessor 12, or be connected to the chip. External memory and update storage may be connected with a serial peripheral interface (SPI). A crystal oscillator may perform RTC capabilities, or act as a secondary check for the processor 12. In addition a JTAG (joint test action group) or SWD (serial wire debug) Header may be implemented for debugging.

Diagnostics 151 may also be present on the AED monitor 1, for users to interface with the AED monitor. For example, LEDs may be used to show battery and network status of the AED monitor. To maintain low battery usage in the resting state, a button would cause the diagnostics 151 to trigger, thus activating the LED to show the AED monitor's 1 status.

Figure 3:
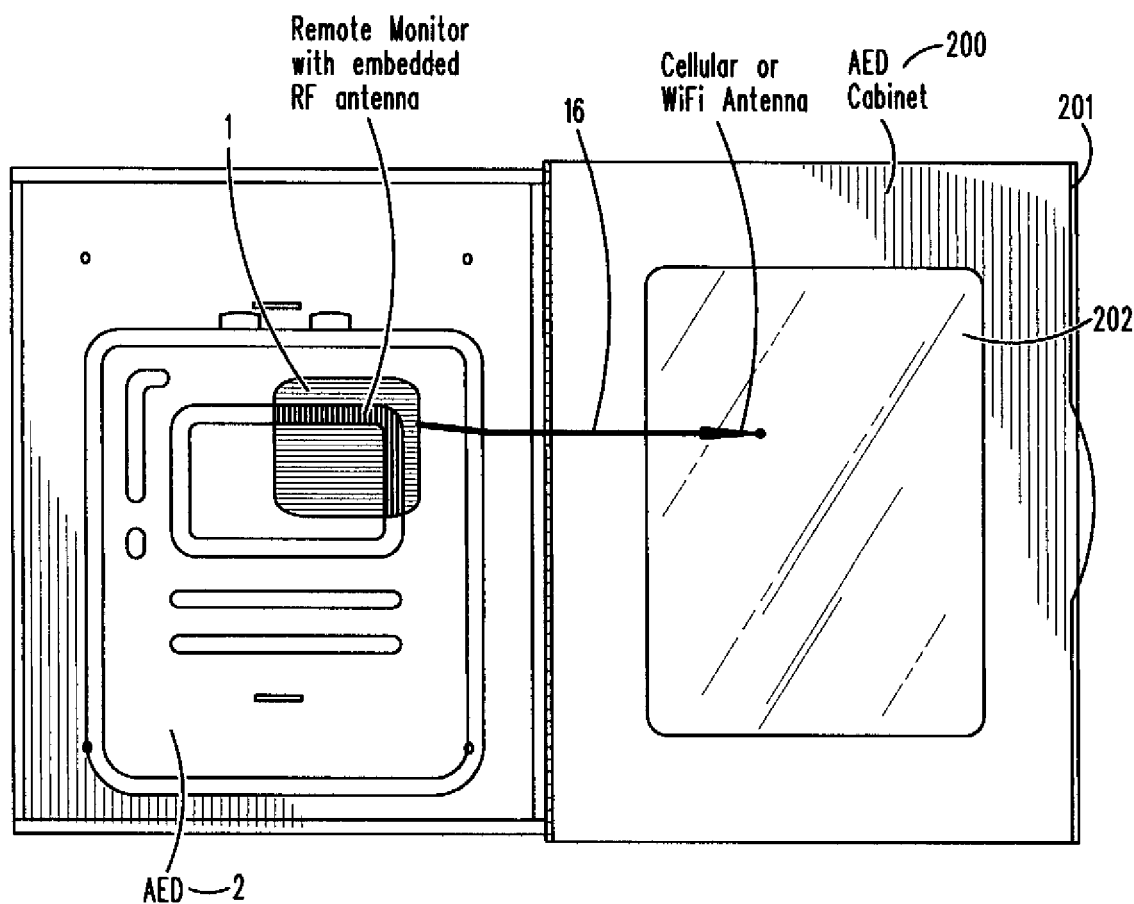
FIG. 3 is a front view of a remote monitor and AED in an AED cabinet according to the present disclosure.

Looking now to FIG. 3 an implementation of AED monitor 1 is shown. Automatic external defibrillator 2 and AED monitor 1 are placed inside a typical AED Cabinet 200. The door 201 is shut and the AED is visible through window 202. In a typical installation a hole is made in the cabinet 200 and antenna 16 is drawn through the cabinet so it is on the exterior. This reduces interference with signals to the AED monitor 1. The monitor 1 is typically placed in the back of the cabinet 200 where it will not interfere with operation of the AED in emergencies.

Figure 4:
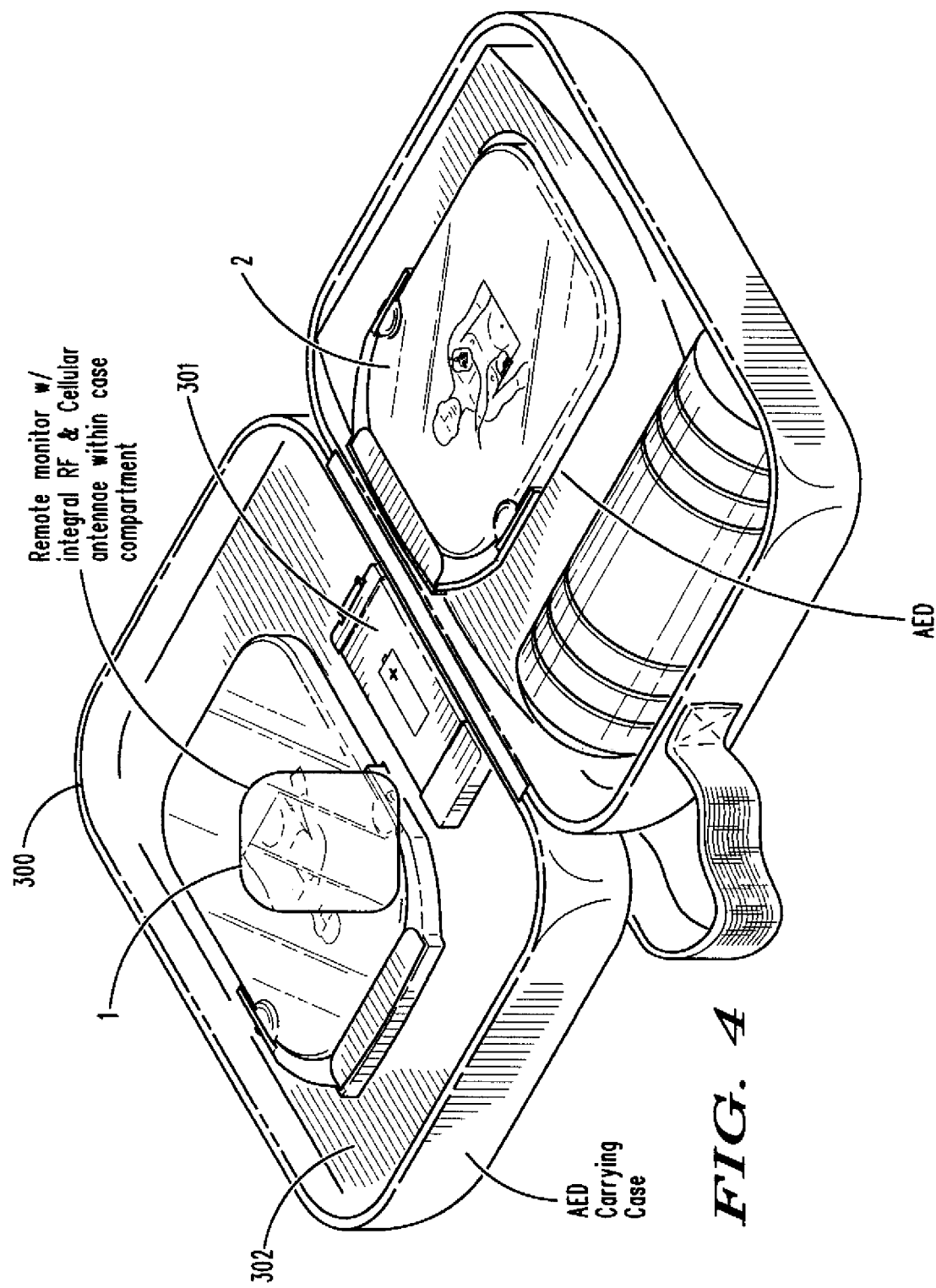
FIG. 4 is a perspective view of a remote monitor and AED in a carrying case.

Looking now to FIG. 4 another implementation of AED monitor 1 is shown. Automatic external defibrillator 2 and AED monitor 1 are placed inside a mobile AED carrying case 300. In a typical case there may be additional batteries 301 and a closable top 302. Some cases cause interference with signals to the AED, however, the AED monitor 1 according to the present invention has several advantages discussed herein to enable communication outside case 300. The monitor 1 is typically placed in case 300 where it will not interfere with operation of the AED in emergencies.

Figure 5:
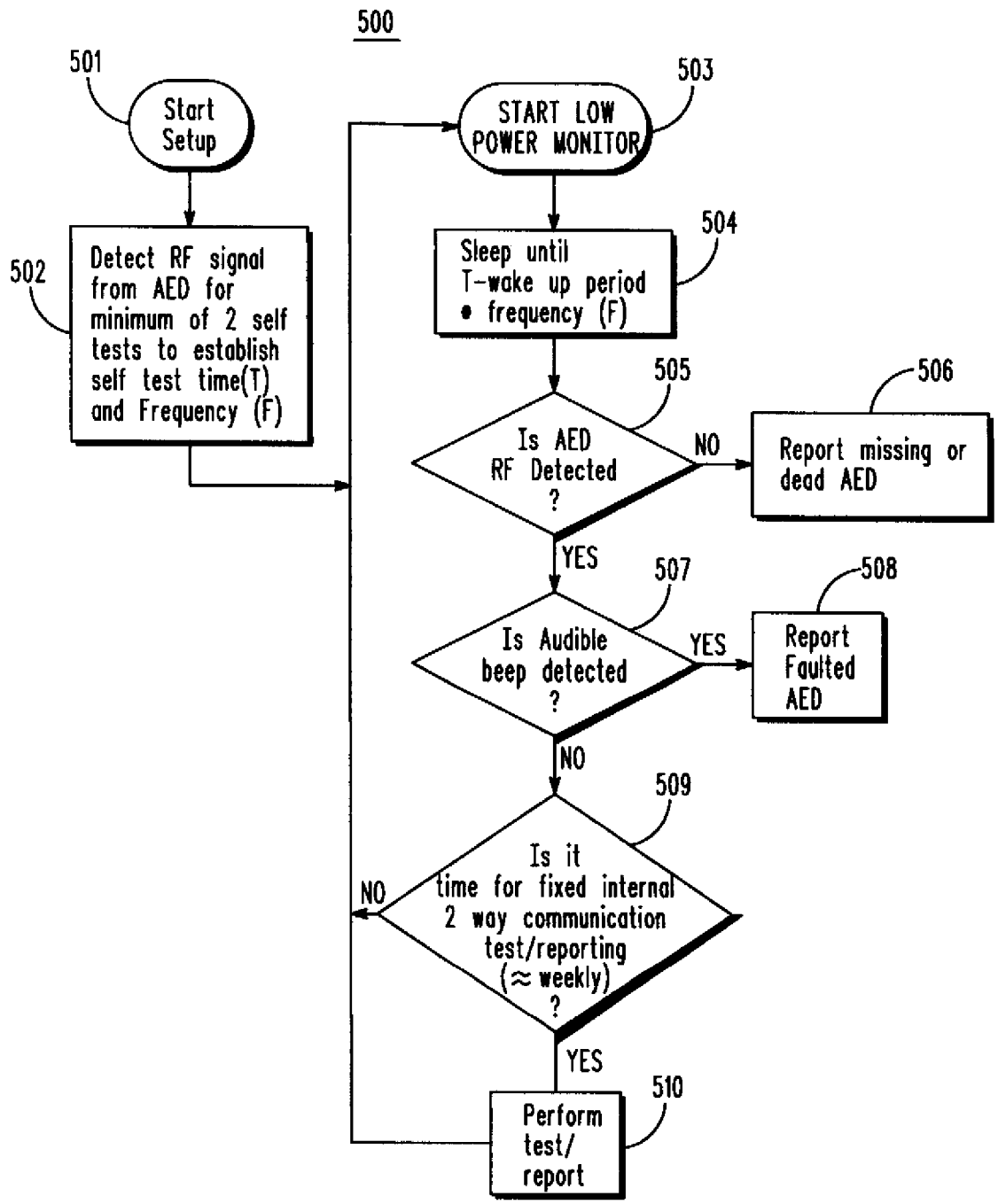
FIG. 5 is a flowchart and decision tree for the AED monitoring system according to the present disclosure.

FIG. 5, essentially illustrates a method 500 of operation for AED monitor 1. After installation into a cabinet 300, bag 400, or other AED installation, AED monitor 1 should begin the setup/startup processes. The startup process then begins to detect electromagnetic (RF) signals from the AED 502. This process can be improved by manually entering values into the monitor 1 prior to installation. However, the monitor can be installed without pre-programming, in such cases the AED monitor 1 then detects electromagnetic signals from the AED for a minimum of 2 self tests which then allows it to establish a time (T) that the AED conducts self tests, and a frequency (F) that it conducts tests. After T and F are established, the monitor then moves to start low-power monitoring 503 of the AED. To enable low power monitoring, the monitor 1 then sleeps 504 until the Time (T) for waking up using the T & F variables stored previously. The monitor 1 then inquires whether the AED's electromagnetic signal is detected 505, if not the AED is reported as missing or dead 506. If an electromagnetic signal is detected the monitor 1 listens for an audible beep 507, if the correct beep or beep sequence is detected the monitor reports the AED is in a fault state 508. If no beep is detected, the monitor 1 inquires whether it is time for a fixed 2-way communication with a remote monitor 509, typically this is done on a weekly basis, but may be adjusted to a bi-weekly or monthly basis to save battery, if it is not time the monitor 1 returns to low power monitoring 503, if it is time to report, then a report is issued 510, then the monitor 1 returns to low-power monitoring.

Such illustrations are illustrative in nature and do not encompass all of the possible angles and types of components utilized in AED monitors according to this disclosure.

INDUSTRIAL APPLICABILITY

The All AEDs turn on at a selected interval for a self inspection. Most turn on every 24 hours for a quick check, every week for a more thorough self inspection, and every month for a complete inspection. These inspections not only check the batteries and pads, but also the internal functions of the AED including the charge circuitry. Following these inspections a pass or fail visual indicator is set, as well as a periodic beep in a fault state.

Utilizing this, a basic method of operation contemplated by the AED monitor 1 of the present disclosure is as follows: 1) Wake up the monitoring system 1 just prior to scheduled AED self inspection; 2) Sense the turn on of the AED for its self inspection with electromagnetic monitor 15; 3) Listen with microphone 14 for a fault signal for a defined period of time, and if the fault signal is discovered a fault condition is present; 4) Report via wireless communication (Wi-Fi, Bluetooth, RF, etc) over antenna 16 the outcome of monitoring; 5) Return monitoring system to battery 13 conservation, sleep mode.

To elaborate more on how typical AEDs 2 work and allows the monitor 1 to detect the default state of an AED; all AEDs go through a self test on a regular schedule. Most go through a 24 hour functional test that requires only minimal current draw from the battery. Most AEDs also go through a more extensive weekly test, often charging the capacitors to a percentage of their full capacity and discharging. Additionally, most AEDs go through a 4 week or monthly extensive self test where they fully charge and discharge the capacitors. It is this periodic turn on period that allows our interference sensing coil 16 to determine if the AED is present and if the AED battery has sufficient power to turn on. A useful aspect of the AED self check is that it turns on at a predetermined periodic interval. For example, a common AED known to one skilled in the art turns on daily at 3:03 am. By knowing the specific timing of every AED, the user can enter the AED type on setup, allowing the electronics to sleep up to the point of test, and turn back off immediately after, preserving battery life 13. In addition, all AEDs will transmit a periodic beep if they detect a problem during their self test Microphone 14 listens for this periodic beep that will be used immediately following the positive output from the interference coil to determine the status of the AED, other than missing or a completely dead battery.

Installation of AED monitor 1 is kept simple so AED technicians can easily install a monitor. Installation and setup can typically be done by the installer's phone through Bluetooth. Wi-Fi connection and setup parameters can be done using a phone application. Setup parameters may include AED model, Wi-Fi selection, fault communication method and phone/address, etc.

Accordingly, although the invention has been described by reference to certain preferred and alternative embodiments, it is not intended that the novel arrangements be limited thereby, but that modifications thereof are intended to be included as falling within the broad scope and spirit of the foregoing disclosures and the appended drawings.

I claim:

1. A combination automated external defibrillator (AED) and AED Monitoring system comprising:
    an AED, the AED having a self-diagnostic subroutine and performing said subroutine at regular intervals, the AED having at least an audio indicator that indicates the results of the self-diagnostic when the diagnosis is that the AED is in need of maintenance; and
    a remote AED monitoring system, the AED monitoring system having a microphone, battery, microprocessor, and wireless communication device, wherein the microprocessor selectively powers up the AED monitoring system prior to the AED's self-diagnostic subroutine and utilizes the microphone to monitor for the AED's audio indicator that the AED is in need of maintenance, and the microprocessor transmitting a wireless signal through the wireless communication device to a remote location indicating whether the AED is in need of maintenance; the microprocessor selectively moving the AED monitoring system from an activated state to a low power state after transmitting the wireless signal; and
    wherein the AED monitor is configured by maintaining the AED monitor in an active state to detect a radio frequency (RF) signal inherently emanating from the AED, the RF signal being electric fields emanating from the AED caused by the turning on of the AED's self-diagnostic subroutine, and using said RF signal to configure the monitor to determine future low power and active states, and wherein the AED monitor low power and active states are synchronized to the AED's self-diagnostic subroutine.

2. The combination of claim 1 wherein the AED monitoring system further comprises an RF antenna, the antenna being a multi-turn coil for sensing RF generated by the AED; the microprocessor monitoring the antenna to verify that the AED is present and that the AED battery is not dead.

3. The combination of claim 2 further comprising a remote online monitoring system, the online monitoring system receiving transmissions from the AED monitoring system and reporting to a user whether the AED is in need of maintenance.

4. The combination of claim 3 further comprising an AED cabinet:
    the AED cabinet encasing the AED and the AED monitoring device;

the wireless communication device mounted to the AED cabinet and connected to the remaining portions of the AED monitor.

5. The combination of claim 3 further comprising an AED bag, the AED bag containing the AED and the AED monitor.

6. The combination of claim 3 wherein:
the AED monitor is initially maintained in the active state for a regular period, and then returns to the low power state.

7. The combination of claim 1 wherein the battery on the AED monitor can maintain sufficient charge for operation for at least five (5) years without recharging while the AED monitor is in normal use.

8. A method for monitoring and reporting the state of an automated external defibrillator (AED) comprising:
providing an AED and an AED monitor;
detecting a signal from the AED to establish a time and an interval when the AED conducts a self-diagnostic test;
placing the AED monitor in a low power state;
maintaining the AED monitor in a low power state;
powering up the AED monitor into an active state at a selected time before the AED conducts the self-diagnostic test;
detecting an electromagnetic signal from the AED;
detecting an audible signal from the AED;
wirelessly reporting a state of the AED to an online monitoring system, the state of the AED determined by the electromagnetic signal from the AED and the audible signal from the AED; and
returning the AED monitor to the low power state.

9. The method of claim 8 wherein:
the AED and the AED monitor are preprogrammed with corresponding information which determines the time when the AED monitor will power up and when the AED will perform the self-diagnostic test.

10. The method of claim 8 further comprising:
installing the AED monitor in an unconfigured state; and
configuring the AED monitor by maintaining the AED monitor in an active state for a period of at least 24 hours and detecting electromagnetic signals from the AED to determine the time the AED conducts self-diagnostic tests, thereby configuring the AED monitor.

11. The method of claim 10 wherein the AED is configured to perform regular self-diagnostic tests at 24 hour intervals and reports the result of said tests via audio beeps.

12. The method of claim 11 wherein the AED monitor comprises:
an electromagnetic coil, the coil being a multi-turn coil, the coil capable of sensing an electromagnetic field generated by the AED; and
a microphone capable of detecting audible beeps from the AED.

13. The method of claim 12 further comprising:
configuring the online monitoring system with a AED monitor identification number and password.

14. The method of claim 13 further comprising:
synchronizing the AED monitor and online monitoring system at a regular interval via two-way communications.

15. The method of claim 14 wherein the synchronizing is performed weekly.

16. A remote monitor for an automated external defibrillator (AED), the remote monitor comprising:
a case;
a communication antenna;
a microphone;
a battery;
an RF antenna, for detecting electromagnetic fields emanating from the AED caused by the AED turning on for its self inspection;
a microprocessor connected to and receiving input from the communication antenna, the communication antenna being in communication with a remote monitor, microphone, and electromagnetic coil, the microprocessor receiving power from the battery selectively outputting signals over the communication antenna; the microprocessor capable of selectively activating and deactivating the remote monitor at a selected interval and time, those intervals and times independent of the amount of charge remaining in the battery, the selected interval and time corresponding to preprogrammed diagnostics conducted by the AED; and
wherein the remote monitor is configured by maintaining the remote monitor in an active state at least until an AED conducts at least one self test and detecting RF signals, including noise inherently emanating from the AED and automated sounds from the AED to determine the time the AED conducts self-diagnostic tests; thereby synchronizing the AED monitor's active and inactive states with an AED.

17. The remote monitor of claim 16 wherein the case comprises:
a width of three and a half inches (3.5") or less;
a height of three and a half inches (3.5") or less; and
a depth of one and one half inch (1.5") or less.

18. The remote monitor of claim 16 wherein the RF antenna a multi-turn coil, the coil capable of sensing an RF generated by an AED.

19. The remote monitor of claim 16 wherein the microprocessor stores information gathered from the electromagnetic coil and microphone for a preselected time interval before transmitting the data to a remote system.

* * * * *